United States Patent
Fitting et al.

(10) Patent No.: US 6,537,932 B1
(45) Date of Patent: *Mar. 25, 2003

(54) STERILIZATION WRAP, APPLICATIONS THEREFOR, AND METHOD OF STERILIZING

(75) Inventors: Steven Wayne Fitting, Acworth, GA (US); Michael David Powers, Canton, GA (US); Roger Bradshaw Quincy, III, Cumming, GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/168,281

(22) Filed: Oct. 8, 1998

Related U.S. Application Data

(63) Continuation-in-part of application No. 08/976,108, filed on Nov. 21, 1997.
(60) Provisional application No. 60/063,878, filed on Oct. 31, 1997.

(51) Int. Cl.[7] .......................... B32B 27/02; B32B 27/16; B05D 3/00; A61L 2/14; A61L 2/26
(52) U.S. Cl. ..................... 442/114; 442/110; 427/538; 427/393.1; 427/2.31; 206/363; 206/439; 422/294
(58) Field of Search ................................. 442/114, 110; 427/532, 535, 538, 384, 389.9, 393.1, 2.31; 206/363, 439; 422/292, 294, 300

(56) References Cited

U.S. PATENT DOCUMENTS 668,791 A    2/1901   Blake et al.

(List continued on next page.)

FOREIGN PATENT DOCUMENTS

| CA | 803714 | 1/1969 | ..................... 28/5 |
| CA | 1188452 | 6/1985 | |

(List continued on next page.)

OTHER PUBLICATIONS

PCT International Search Report No.: PCT/US 98/23071, mailed Apr. 18, 1999.

(List continued on next page.)

*Primary Examiner*—Cheryl A. Juska
(74) *Attorney, Agent, or Firm*—Dority & Manning, PA

(57) ABSTRACT

A method of preparing a sterilized nonwoven web, which method includes providing a nonwoven web; coating the nonwoven web with from about 0.005 to about 3 percent by weight, based on the weight of the web, of an antistatic agent; and exposing the coated nonwoven web to an oxidizing gas plasma. The antistatic agent is adapted to be free of a malodor after exposure of the coated nonwoven web to the oxidizing gas plasma. The antistatic agent may be further adapted to provide a sterilized nonwoven web having a hydrohead value as measured by Method 5514 of Federal Test Method Standard No. 191A which is at least 50 percent of the hydrohead value of the coated nonwoven web before exposure to the oxidizing gas plasma. The antistatic agent also may be adapted to provide a sterilized nonwoven web having a surface resistivity in ohms which is lower than the surface resistivity in ohms of the coated nonwoven web before exposure of the coated nonwoven web to the oxidizing gas plasma. The antistatic agent may be an alkali metal or ammonium salt of either a mono- or di-$C_3$-alkyl phosphate in which the $C_3$-alkyl moiety is an alkyl group containing three carbon atoms optionally substituted with hydroxy groups or a $\beta$-carbon substituted alkyl phosphate, a di($\beta$-carbon substituted alkyl) phosphate, or a mixture of two or more of the foregoing. The invention also provides a fibrous sheet-like material, such as a barrier fabric, a sterilization wrap, a surgical garment, and medical procedure packs.

20 Claims, 3 Drawing Sheets

U.S. PATENT DOCUMENTS

| | | | |
|---|---|---|---|
| 813,063 A | 5/1906 | Sutton et al. | |
| 859,998 A | 7/1907 | Wentworth | |
| 924,032 A | 6/1909 | Blake | |
| 1,222,305 A | 4/1917 | Kraus | |
| 1,297,159 A | 3/1919 | Hedberg | |
| 1,355,477 A | 10/1920 | Howell | |
| 2,106,865 A | 2/1938 | Bantz et al. | |
| 2,217,444 A | 10/1940 | Hill | |
| 2,328,577 A | 9/1943 | Oglesby | |
| 2,398,792 A | 4/1946 | Johnson | |
| 2,738,067 A | 3/1956 | Cook, Jr. | |
| 2,748,018 A | 5/1956 | Miller | |
| 2,998,051 A | 8/1961 | Sittel | 154/1.7 |
| 3,012,668 A | 12/1961 | Fraas | |
| 3,059,772 A | 10/1962 | Baron | 209/127 |
| 3,125,547 A | 3/1964 | Blatz | 260/45.5 |
| 3,276,944 A | 10/1966 | Levy | 161/150 |
| 3,281,347 A | 10/1966 | Winder | 204/168 |
| 3,323,933 A | 6/1967 | Barford et al. | |
| 3,338,992 A | 8/1967 | Kinney | 264/24 |
| 3,341,007 A | 9/1967 | Mayer et al. | 209/2 |
| 3,341,394 A | 9/1967 | Kinney | |
| 3,349,285 A | 10/1967 | Belkin | 317/2 |
| 3,380,584 A | 4/1968 | Fulwyler | 209/3 |
| 3,402,814 A | 9/1968 | Morel et al. | 209/127 |
| 3,436,797 A | 4/1969 | Graf et al. | 156/272.6 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,571,679 A | 3/1971 | Turnout | 317/262 |
| 3,581,886 A | 6/1971 | Singewald et al. | 209/9 |
| 3,692,606 A | 9/1972 | Miller et al. | 156/273.1 |
| 3,692,618 A | 9/1972 | Dorschner et al. | |
| 3,711,898 A | 1/1973 | Debbas | |
| 3,802,817 A | 4/1974 | Matsuki et al. | 425/66 |
| 3,821,021 A * | 6/1974 | McMillin | 117/135.5 |
| 3,849,241 A | 11/1974 | Butin et al. | |
| 3,855,046 A | 12/1974 | Hansen | |
| 3,859,330 A | 1/1975 | Proskow | 260/47 UA |
| 3,896,802 A | 7/1975 | Williams | 128/156 |
| 3,907,604 A | 9/1975 | Prentice | 136/146 |
| 3,909,009 A | 9/1975 | Cvetko et al. | 274/37 |
| 3,962,386 A | 6/1976 | Driscoll | 264/22 |
| 3,979,529 A | 9/1976 | Rebentisch et al. | 427/25 |
| 3,998,916 A | 12/1976 | van Turnhout | 264/22 |
| 4,011,067 A | 3/1977 | Carey, Jr. | 55/354 |
| 4,013,816 A | 3/1977 | Sabee et al. | 428/288 |
| 4,035,164 A | 7/1977 | Taylor | |
| 4,041,203 A | 8/1977 | Brock et al. | 428/157 |
| 4,058,724 A | 11/1977 | McKinney et al. | |
| 4,070,218 A | 1/1978 | Weber | 156/167 |
| 4,091,140 A | 5/1978 | Harmon | |
| 4,096,289 A | 6/1978 | Nischwitz et al. | 428/283 |
| 4,103,062 A | 7/1978 | Aberson et al. | 428/283 |
| 4,140,607 A | 2/1979 | Kreiseimeier et al. | 204/168 |
| 4,144,538 A | 3/1979 | Chapman et al. | |
| 4,170,304 A | 10/1979 | Huke | |
| 4,178,157 A | 12/1979 | van Turnhout et al. | 55/155 |
| 4,185,972 A | 1/1980 | Nitta et al. | |
| 4,196,245 A | 4/1980 | Kitson et al. | 428/198 |
| 4,208,366 A | 6/1980 | Kinney | |
| 4,209,563 A | 6/1980 | Sisson | 428/288 |
| 4,215,682 A | 8/1980 | Kubik et al. | 128/205.29 |
| 4,223,677 A | 9/1980 | Anderson | 128/287 |
| 4,273,635 A | 6/1981 | Beraud et al. | 204/165 |
| RE30,782 E | 10/1981 | van Turnhout | 264/22 |
| 4,298,440 A | 11/1981 | Hood | 204/165 |
| 4,305,797 A | 12/1981 | Knoll et al. | |
| 4,307,143 A | 12/1981 | Meitner | 252/91 |
| 4,308,223 A | 12/1981 | Stern | 264/22 |
| 4,310,478 A | 1/1982 | Balslev et al. | |
| 4,323,374 A | 4/1982 | Shinagawa et al. | |
| 4,324,198 A | 4/1982 | Muz | 118/630 |
| 4,340,563 A | 7/1982 | Appel et al. | 264/518 |
| 4,342,812 A | 8/1982 | Selwood | 428/286 |
| 4,353,799 A | 10/1982 | Leonard | 210/321.3 |
| 4,357,234 A | 11/1982 | Inculet et al. | |
| 4,363,682 A | 12/1982 | Thiebault | |
| 4,363,723 A | 12/1982 | Knoll et al. | |
| 4,373,224 A | 2/1983 | Bandai et al. | |
| 4,374,727 A | 2/1983 | Takahashi et al. | |
| 4,374,888 A | 2/1983 | Bornslaeger | 428/198 |
| 4,375,718 A | 3/1983 | Wadsworth et al. | 29/592 |
| RE31,285 E | 6/1983 | van Turnhout et al. | 55/155 |
| 4,392,876 A | 7/1983 | Schmidt | |
| 4,394,235 A | 7/1983 | Brandt et al. | |
| 4,411,795 A | 10/1983 | Olson | 210/679 |
| 4,430,277 A | 2/1984 | Lin | |
| 4,443,513 A | 4/1984 | Meitner et al. | 422/195 |
| 4,443,515 A | 4/1984 | Atlas | 428/224 |
| 4,451,589 A | 5/1984 | Morman et al. | 523/124 |
| 4,455,195 A | 6/1984 | Kinsley | 162/13 |
| 4,455,237 A | 6/1984 | Kinsley | 210/767 |
| 4,456,648 A | 6/1984 | Adamse et al. | 428/283 |
| 4,492,633 A | 1/1985 | Sandulyak et al. | |
| 4,507,539 A | 3/1985 | Sando et al. | 219/121 PY |
| 4,513,049 A | 4/1985 | Yamasaki et al. | |
| 4,514,289 A | 4/1985 | Inculet | |
| 4,517,143 A | 5/1985 | Kisler | |
| 4,534,918 A | 8/1985 | Forrest, Jr. | |
| 4,547,420 A | 10/1985 | Krueger et al. | |
| 4,551,378 A | 11/1985 | Carey, Jr. | 428/198 |
| 4,554,207 A | 11/1985 | Lee | 428/288 |
| 4,555,811 A | 12/1985 | Shimalla | 2/51 |
| 4,588,537 A | 5/1986 | Klaase et al. | 264/22 |
| RE32,171 E | 6/1986 | van Turnhout | 55/155 |
| 4,592,815 A | 6/1986 | Nakao | 204/165 |
| 4,594,626 A | 6/1986 | Frangesh | |
| 4,618,524 A | 10/1986 | Groitzsch et al. | 428/198 |
| 4,622,259 A | 11/1986 | McAmish et al. | 428/171 |
| 4,623,438 A | 11/1986 | Felton et al. | 204/168 |
| 4,626,263 A | 12/1986 | Inoue et al. | |
| 4,652,282 A | 3/1987 | Ohmori et al. | 55/155 |
| 4,652,322 A | 3/1987 | Lim | 156/181 |
| 4,657,639 A | 4/1987 | Mahadevan et al. | |
| 4,657,804 A | 4/1987 | Mays et al. | 428/212 |
| 4,663,220 A | 5/1987 | Wisneski et al. | 428/221 |
| 4,670,913 A | 6/1987 | Morell et al. | 2/227 |
| 4,671,943 A | 6/1987 | Wahlquist | |
| 4,677,017 A | 6/1987 | DeAntonis et al. | 428/214 |
| 4,689,241 A | 8/1987 | Richart et al. | 427/28 |
| 4,699,823 A | 10/1987 | Kellenberger et al. | |
| 4,705,171 A | 11/1987 | Eldridge | |
| 4,707,398 A | 11/1987 | Boggs | 428/224 |
| 4,714,647 A | 12/1987 | Shipp, Jr. et al. | 428/212 |
| 4,720,415 A | 1/1988 | Vander Wielen et al. | 428/152 |
| 4,729,731 A | 3/1988 | Krueger et al. | |
| 4,738,772 A | 4/1988 | Giesfeldt | 209/2 |
| 4,739,882 A | 4/1988 | Parikh et al. | |
| 4,749,348 A | 6/1988 | Klaase et al. | 427/174.8 |
| 4,761,326 A | 8/1988 | Barnes et al. | 428/219 |
| 4,789,504 A | 12/1988 | Ohmori et al. | |
| 4,795,668 A | 1/1989 | Krueger et al. | 428/174 |
| 4,797,201 A | 1/1989 | Kuppers et al. | 209/127.4 |
| 4,797,318 A | 1/1989 | Brooker et al. | |
| 4,818,464 A | 4/1989 | Lau | 264/510 |
| 4,826,703 A | 5/1989 | Kisler | 427/466 |
| 4,831,664 A | 5/1989 | Suda | |
| 4,847,914 A | 7/1989 | Suda | |
| 4,859,266 A | 8/1989 | Akasaki et al. | 156/372.1 |
| 4,863,785 A | 9/1989 | Berman et al. | 428/218 |

| | | | | | | |
|---|---|---|---|---|---|---|
| 4,863,983 A | 9/1989 | Johnson et al. ............. 524/140 | | 5,389,202 A | 2/1995 | Everhart et al. ............ 162/103 |
| 4,874,399 A | 10/1989 | Reed et al. ...................... 55/2 | | 5,397,413 A | 3/1995 | Trimble et al. ............. 156/167 |
| 4,874,659 A | 10/1989 | Ando et al. ................. 428/221 | | 5,401,446 A | 3/1995 | Tsai et al. ...................... 264/22 |
| 4,883,052 A | 11/1989 | Weiss et al. | | 5,407,581 A | 4/1995 | Onodera et al. ............ 210/654 |
| 4,886,527 A | 12/1989 | Fottinger et al. ............. 55/156 | | 5,409,766 A | 4/1995 | Yuasa et al. ................. 428/224 |
| 4,894,131 A | 1/1990 | Jacobs et al. ............... 204/165 | | 5,411,576 A | 5/1995 | Jones et al. ..................... 95/57 |
| 4,901,370 A | 2/1990 | Suda | | 5,436,033 A | 7/1995 | Mino et al. |
| 4,904,174 A | 2/1990 | Moosmayer et al. | | 5,436,066 A | 7/1995 | Chen .......................... 428/288 |
| 4,917,942 A | 4/1990 | Winters | | 5,441,550 A | 8/1995 | Hassenboehler, Jr. ........ 55/486 |
| 4,920,168 A | 4/1990 | Nohr et al. ................. 524/188 | | 5,443,606 A | 8/1995 | Hassenboehler, Jr. ........ 55/486 |
| 4,944,854 A | 7/1990 | Felton et al. ............... 204/168 | | 5,455,108 A | 10/1995 | Quincy et al. ............. 428/266 |
| 4,948,515 A | 8/1990 | Okumura et al. ........... 210/748 | | 5,456,972 A | 10/1995 | Roth et al. ................... 428/224 |
| 4,948,639 A | 8/1990 | Brooker et al. ............ 428/35.2 | | 5,464,678 A * | 11/1995 | Mudge et al. ................ 428/96 |
| 4,960,820 A | 10/1990 | Hwo .......................... 524/528 | | 5,464,688 A | 11/1995 | Timmons et al. |
| 4,965,122 A | 10/1990 | Morman ..................... 428/225 | | 5,468,428 A | 11/1995 | Hanschen et al. |
| 4,983,677 A | 1/1991 | Johnson et al. ............. 525/127 | | 5,472,481 A | 12/1995 | Jones et al. ..................... 96/15 |
| 5,012,094 A | 4/1991 | Hamade | | 5,482,765 A | 1/1996 | Bradley et al. |
| 5,021,501 A | 6/1991 | Ohmori et al. ............. 524/544 | | 5,486,411 A | 1/1996 | Hassenboehler, Jr. ........ 428/286 |
| 5,032,419 A | 7/1991 | Lamirand et al. ............. 427/25 | | 5,491,022 A | 2/1996 | Smith .......................... 428/224 |
| 5,035,941 A | 7/1991 | Blackburn .................. 428/286 | | 5,491,026 A * | 2/1996 | Mudge et al. ............. 428/395 |
| 5,051,159 A | 9/1991 | Togashi et al. ............. 204/165 | | 5,493,117 A | 2/1996 | Tamaki et al. ............... 264/483 |
| 5,055,151 A | 10/1991 | Duffy | | 5,496,507 A | 3/1996 | Angadjivand et al. ...... 264/423 |
| 5,057,710 A | 10/1991 | Nishiura et al. ............ 307/400 | | 5,503,745 A | 4/1996 | Ogata et al. ................. 210/490 |
| 5,062,158 A | 11/1991 | Oka et al. ......................... 2/46 | | 5,540,953 A * | 7/1996 | Harrington ............... 427/393.5 |
| 5,077,468 A | 12/1991 | Hamade | | 5,552,012 A | 9/1996 | Morris et al. ............. 156/272.4 |
| 5,090,975 A | 2/1992 | Requejo et al. | | 5,592,357 A | 1/1997 | Rader et al. |
| 5,102,738 A | 4/1992 | Bell et al. | | 5,620,785 A | 4/1997 | Watt et al. ................... 428/219 |
| 5,110,620 A | 5/1992 | Tani et al. ..................... 427/40 | | 5,627,376 A | 5/1997 | Jaisinghani et al. ........ 250/325 |
| 5,112,677 A | 5/1992 | Tani et al. ................... 428/240 | | 5,637,165 A | 6/1997 | Chen .......................... 156/62.2 |
| 5,112,690 A | 5/1992 | Cohen et al. | | 5,643,524 A | 7/1997 | De Cauwer et al. |
| 5,118,942 A | 6/1992 | Hamade ..................... 250/324 | | 5,643,525 A | 7/1997 | McGinty et al. |
| 5,122,048 A | 6/1992 | Deeds | | 5,667,562 A | 9/1997 | Midkiff |
| 5,135,724 A | 8/1992 | Dinter et al. | | 5,686,050 A | 11/1997 | Wadsworth et al. |
| 5,138,971 A | 8/1992 | Nakajima et al. | | 5,688,157 A | 11/1997 | Bradley et al. ............. 442/340 |
| 5,143,767 A | 9/1992 | Matsuura et al. | | 5,688,465 A | 11/1997 | Myers |
| 5,149,335 A | 9/1992 | Kellenberger et al. ...... 604/372 | | 5,709,735 A | 1/1998 | Midkiff et al. |
| 5,156,902 A | 10/1992 | Pieper et al. ............... 604/370 | | 5,721,180 A | 2/1998 | Shipp et al. |
| 5,165,539 A * | 11/1992 | Weber et al. ............... 206/363 | | 5,730,923 A | 3/1998 | Hassenboehler |
| 5,165,979 A | 11/1992 | Watkins et al. ............. 428/113 | | 5,736,473 A | 4/1998 | Cohen et al. ................. 442/239 |
| 5,169,706 A | 12/1992 | Collier, IV et al. ......... 428/152 | | 5,762,857 A | 6/1998 | Weng et al. |
| 5,173,356 A | 12/1992 | Eaton et al. ................ 428/219 | | 5,807,366 A | 9/1998 | Milani |
| 5,178,932 A | 1/1993 | Perkins et al. ............. 428/198 | | 5,814,570 A | 9/1998 | Cohen |
| 5,183,701 A | 2/1993 | Jacobs et al. ............... 428/229 | | 5,817,584 A | 10/1998 | Singer et al. |
| 5,188,885 A | 2/1993 | Timmons et al. ........... 428/198 | | 5,821,178 A | 10/1998 | Cohen |
| 5,204,174 A | 4/1993 | Daponte et al. ............ 428/286 | | 5,830,810 A * | 11/1998 | Cohen ........................ 442/110 |
| 5,206,061 A | 4/1993 | Ando et al. ................. 428/34.7 | | 5,834,384 A | 11/1998 | Cohen et al. |
| 5,213,881 A | 5/1993 | Timmons et al. ........... 428/224 | | 5,834,386 A | 11/1998 | Cohen |
| 5,213,882 A | 5/1993 | Sassa et al. ................. 428/224 | | 5,873,968 A | 2/1999 | Shipp et al. |
| 5,225,018 A | 7/1993 | Zeldin et al. | | 5,877,099 A | 3/1999 | Cohen |
| 5,226,992 A | 7/1993 | Morman ..................... 156/62.4 | | | | |
| 5,227,172 A | 7/1993 | Deeds | | | FOREIGN PATENT DOCUMENTS | |
| 5,230,727 A | 7/1993 | Pound et al. ................. 55/492 | EP | 0 125 851 | 11/1984 | |
| 5,232,770 A | 8/1993 | Joseph ....................... 428/284 | EP | 0 156 160 | 10/1985 | |
| 5,238,733 A | 8/1993 | Joseph et al. ............... 428/284 | EP | 0 245 108 | 11/1987 | |
| 5,244,482 A | 9/1993 | Hassenboehler, Jr. ........ 55/528 | EP | 0 334 829 | 9/1989 | |
| 5,246,637 A | 9/1993 | Matsuura et al. | EP | 0 337 662 | 10/1989 | |
| 5,247,072 A | 9/1993 | Ning et al. ................... 536/97 | EP | 0 375 234 | 6/1990 | |
| 5,254,297 A | 10/1993 | Deeds | EP | 0 391 725 | 10/1990 | |
| 5,256,176 A | 10/1993 | Mastuura et al. ............ 55/528 | EP | 0 444 671 | 9/1991 | |
| 5,257,982 A | 11/1993 | Cohen et al. ............... 604/348 | EP | 0 462 574 | 12/1991 | |
| 5,264,276 A | 11/1993 | McGregor et al. .......... 428/252 | EP | 0 478 011 | 4/1992 | |
| 5,284,703 A | 2/1994 | Everhart et al. ............ 428/283 | EP | 0 520 798 | 12/1992 | |
| 5,286,326 A | 2/1994 | Greve ..................... 156/272.4 | EP | 0 550 029 | 7/1993 | |
| 5,288,460 A * | 2/1994 | Caputo et al. ................. 422/23 | EP | 0 557 024 A | 8/1993 | |
| 5,294,482 A | 3/1994 | Gessner | EP | 0 575 629 | 12/1993 | |
| 5,306,534 A | 4/1994 | Bosses ...................... 428/35.2 | EP | 0 576 738 | 1/1994 | |
| 5,308,674 A | 5/1994 | Zafiroglu ................... 428/102 | EP | 0 594 123 | 4/1995 | |
| 5,308,691 A | 5/1994 | Lim et al. ................... 428/286 | EP | 0 729 161 | 8/1996 | |
| 5,336,545 A | 8/1994 | Morman ..................... 428/152 | EP | 0 754 796 | 1/1997 | |
| 5,350,620 A | 9/1994 | Sundet et al. ............... 428/172 | GB | 2 026 379 | 2/1980 | |
| 5,382,400 A | 1/1995 | Pike et al. .................. 264/168 | GB | 2 242 142 | 9/1991 | |

| | | |
|---|---|---|
| JP | 58-076118 | 7/1958 |
| JP | 62-053719 | 8/1987 |
| JP | 62-074423 | 9/1987 |
| JP | 1-246413 | 10/1989 |
| JP | 5-064713 | 3/1993 |
| WO | 81/03265 | 11/1981 |
| WO | 90/11784 | 10/1990 |
| WO | 91/08254 | 6/1991 |
| WO | 92/16681 | 10/1992 |
| WO | 93/06168 | 4/1993 |
| WO | 93/09156 | 5/1993 |
| WO | 94/00166 | 1/1994 |
| WO | 94/01068 | 1/1994 |
| WO | 95/05232 | 2/1995 |
| WO | 95/05501 | 2/1995 |
| WO | 95/22646 | 8/1995 |
| WO | 96/00093 | 1/1996 |
| WO | 96/28597 | 9/1996 |
| WO | 97/04155 | 2/1997 |
| WO | 97/04155 A | 2/1997 |

OTHER PUBLICATIONS

An introduction to Electrostatic Separation, Technical Bulletin, Bulletin 8570, Carpco, Inc.
Electrostatic Separation of Mixed Granular Solids by Oliver C. Ralston, Elsevier Publishing Company, 1961, Chapter IV, "Applications of Electrostatic Separation", pp. 134–234.
Abstract of JP–59 094621 dated May 31, 1984.
Abstract of JP–60 209920 dated Oct. 21, 1985.
Abstract of JP–57 105217 dated Jun. 30, 1982.
Abstract of JP–62 102809 dated May 13, 1987.
Abstract of JP–01 156578 dated Jun. 20, 1998.
"Bonding Process", IBM Technical Disclosure Bulletin, vol. 14, No. 12, May 1972.
Journal of Electrostatics, vol. 21, 1988, Amsterdam NL, pp. 81–98, XP002012022, P. A. Smith & G. C. East: "Generations of Triboelectric Charge in Textile Fibre Mistures, and their use as Air Filters", see document.
J. van Turnhout: Topics in Applied Physics, vol. 33, Chapter 3 "Thermally Stimulated Discharge of Electrets", pp. 81–218 (1980).
J. van Turnhout: Thermally Stimulated Discharge of Polymer Electrets, Chapter 1, pp. 1–24 (1975).
G.M. Sessler: "Electronic Properties of Polymers, Chapter 3" Charge Storage, pp. 59–107.
Abstract: "An experimental study of charge distributions in electron–beam irradated polypropylene films." IEEE Transactions on Electrical Insulation, v. 26, n. 2, Apr. 1991, p. 228–235.
Simco® Instruction, Operation, and Maintenance Manual on Chargemaster® Pinner™ Arc Resistant Charging Bar.
K.D. Lawrence, R.T. Lucas, and J.A. Young, "An Improved Device for the Formation of Superfine, Thermoplastic Fibers" U.S. Naval Research Laboratory, Feb. 11, 1959. NRL Report 5265.
V.A. Wente, E.L. Bone, and C.D. Fluharty, "Manufacture of Superfine Organic Fibers" U.S. Naval Research Laboratory, May 25, 1954. NRL Report 4364.

* cited by examiner

STERILIZATION WRAP, APPLICATIONS THEREFOR, AND METHOD OF STERILIZING

This application is a continuation-in-part of copending Application Serial No. 08/976,108, which was filed on Nov. 21, 1997 and claimed priority from Provisional Application Serial No. 60/063,878, filed on Oct. 31, 1997, which applications are incorporated herein by reference.

BACKGROUND OF THE INVENTION

The present invention relates to a nonwoven web which may be sterilized. More specifically, the present invention relates to a sterilization wrap.

Sterilization wrap is a barrier material which is impermeable to liquids and microorganisms, while being permeable to gases. Sterilization wrap typically is manufactured in roll form and subsequently converted to cut sheets of various sizes as required by such end users as hospitals, clinics, and other health care providers. In order to minimize or prevent static buildup during the manufacturing and/or converting processes, an antistatic agent typically is applied to the wrap early in the manufacturing process. In general, the antistatic agent is dissolved or dispersed in water and the resulting aqueous medium is applied to the web by any suitable procedure. For example, the aqueous medium may be applied by spraying, brushing, or dipping and nipping.

The presence of an antistatic agent on the sterilization wrap also is of benefit during the wrapping process. Items to be sterilized, such as surgical instruments, typically are placed in a suitable instrument transport tray and the combination of instruments and tray is wrapped with, for example, two layers of sterilization wrap and the top layer is taped to provide a sealing relationship. Thus, the first wrapping is closed before the second wrapping is applied. This procedure is referred to in the art as sequential wrapping. The presence of a static charge on the sheets may result in more than one sheet being picked up at a time, leading to inefficiency and sometimes increased cost in the wrapping process. However, simultaneous wrapping may be employed and involves wrapping with two sheets of wrap at the same time. In either case, the wrap is designed to permit the entrance of sterilants such as steam or ethylene oxide to sterilize the contents while presenting a barrier to the entrance of contaminants such as bacteria once the sterilization process is complete.

Antistatic agents are, of course, well known in the art. One commercially available antistatic agent which has been used extensively in the past is a mixture of dipotassium butyl phosphate and potassium dibutyl phosphate salts. The material is available from DuPont Chemicals, Wilmington, Delaware, and is described in U.S. Pat. No. 3,821,021 to McMillin as part of a class of antistatic agents. Such class is defined by the formula $M_nR_{3-n}PO_4$, where M is selected from the group consisting of lithium, sodium, potassium, and ammonium ions, R represents an alkyl group containing 3 to 5 carbon atoms, and n is selected from the integers 1 and 2. According to the patent, the preferred agents are those where M represents the potassium ion, and the most highly preferred finish is a mixture of approximately equimolar quantities of potassium dibutyl phosphate and dipotassium butyl phosphate in which the butyl moieties are straight-chain hydrocarbon groups, i.e., n-butyl groups.

When the most highly preferred finish of the above patent is added to a sterilization wrap and treated by one of the more recently developed sterilization processes which utilize an oxidizing gas plasma, the wrap may exhibit one or more of several undesirable characteristics. First, a sharp, acidic odor (referred to hereinafter as a malodor) often is present in the wrap. The term "malodor" is used herein to mean any odor deemed by those using the wrap to be unpleasant or objectionable. Second, the barrier property of the wrap, as measured by hydrohead values, typically is reduced. Third, the antistatic property of the wrap, as measured by surface resistivity, also is reduced; that is, the surface resistivity of the wrap after sterilization is higher than the surface resistivity before sterilization. Accordingly, there is a need for an improved antistatic agent for a sterilization wrap which is to be exposed to an oxidizing gas plasma.

SUMMARY OF THE INVENTION

The present invention is grounded in the discovery that replacing a mixture of approximately equimolar quantities of potassium dibutyl phosphate and dipotassium butyl phosphate with an antistatic agent adapted to be free of a malodor after exposure to an oxidizing gas plasma of a nonwoven web or sterilization wrap coated with the antistatic agent successfully reduces or eliminates malodor. For example, the use of an antistatic agent which involves one or more salts of mono- and di-$C_3$-alkyl phosphates and/or one or more salts of β-carbon substituted mono- and dialkyl phosphates, both defined hereinafter, reduces or eliminates the above-noted undesirable characteristics when the sterilization process involves exposing a sterilization wrap to an oxidizing gas plasma.

Thus, the present invention addresses some of the difficulties and problems discussed above by providing a method of preparing a sterilized nonwoven web. The method includes providing a nonwoven web; coating the nonwoven web with from about 0.005 to about 3 percent by weight, based on the weight of the web, of an antistatic agent; and exposing the coated nonwoven web to an oxidizing gas plasma. The antistatic agent is adapted to be free of malodors after exposure of the coated nonwoven web. The antistatic agent may be further adapted to provide a sterilized nonwoven web having a hydrohead value as measured by Method 5514 of Federal Test Method Standard No. 191A which is at least 50 percent of the hydrohead value of the coated nonwoven web before exposure to the oxidizing gas plasma. The antistatic agent also may be adapted to provide a sterilized nonwoven web having a surface resistivity in ohms which is lower than the surface resistivity in ohms of the coated nonwoven web before exposure of the coated nonwoven web to the oxidizing gas plasma.

By way of example, the antistatic agent may be an alkali metal or ammonium salt of a mono- or di-$C_3$-alkyl phosphate in which the $C_3$-alkyl moiety is an alkyl group containing three carbon atoms optionally substituted with hydroxy groups. Desirable members of this group are the alkali metal and ammonium salts of propyl phosphate, dipropyl phosphate, isopropyl phosphate, and diisopropyl phosphate, or mixtures of two or more of the foregoing. For example, such salt may be a potassium salt.

As another example, the antistatic agent may be an alkali metal or ammonium salt of a β-carbon substituted alkyl phosphate, a di(βcarbon substituted alkyl) phosphate, or a mixture of two or more of the foregoing. The β-carbon substituted alkyl group in general may contain from four to about seven carbon atoms. Desirable members of this group are the alkali metal and ammonium salts of isobutyl phosphate, diisobutyl phosphate, and mixtures of the foregoing. For example, such salt may be a potassium salt.

Also by way of example, the nonwoven web may be a meltblown web. As another example, the meltblown web may be a component of a laminate. For example, the meltblown web may be between and bonded to two spunbond webs.

The present invention further provides a sterilization wrap which includes a gas-permeable, water-impermeable nonwoven web coated with from about 0.005 to about 3 percent by weight, based on the weight of the web, of an antistatic agent. The antistatic agent is adapted, after exposure of the coated water-impermeable nonwoven web to an oxidizing gas plasma, to be free of malodors and to have a hydrohead value as measured by Method 5514 of Federal Test Method Standard No. 191A which is at least 50 percent of the hydrohead value of the coated water-impermeable nonwoven web before exposure to the oxidizing gas plasma. The antistatic agent in general may be that described hereinbefore.

By way of example, the nonwoven web may be a meltblown web. As another example, the meltblown web may be a component of a laminate. As still another example, the meltblown web may be between and bonded to two spunbond webs.

The present invention additionally provides a barrier fabric, a sterilization wrap, and a surgical garment, each composed of the fibrous sheet-like material described hereinabove.

The present invention still further provides a medical procedure pack which includes a fluid permeable container having an exterior and an interior, one or more items to be sterilized which are present in the interior of the container, and one or more layers of sterilization wrap surrounding the exterior of the container in a sealing relationship. The sterilization wrap includes a gas-permeable, water-impermeable nonwoven web coated with from about 0.005 to about 3 percent by weight, based on the weight of the web, of an antistatic agent, wherein the antistatic agent is adapted, after exposure of the coated water-impermeable nonwoven web to an oxidizing gas plasma, to be free of a malodor and to provide a nonwoven web having a hydrohead value as measured by Method 5514 of Federal Test Method Standard No. 191A after exposure to the oxidizing gas plasma which is at least 50 percent of the hydrohead value of the coated water-impermeable nonwoven web before exposure to the oxidizing gas plasma. The antistatic agent may be further adapted to have a surface resistivity in ohms which is lower than the surface resistivity in ohms of the coated water-impermeable nonwoven web before exposure to the oxidizing gas plasma. The antistatic agent and the nonwoven web are as described hereinbefore.

In a variation of the medical procedure pack described above, a container having an exterior and an interior may have one or more items to be sterilized present in the interior of the container, in which at least a portion of the container comprises the gas-permeable, water-impermeable nonwoven web described earlier.

Finally, the present invention provides a method of manufacturing a nonwoven web adapted to be sterilized by exposure to an oxidizing gas plasma. The method involves providing a nonwoven web and coating the nonwoven web with from about 0.005 to about 3 percent by weight, based on the weight of the web, of an antistatic agent. The antistatic agent is adapted to be free of a malodor after exposure of the coated nonwoven web to the oxidizing gas plasma. The antistatic agent may be further adapted to provide a sterilized nonwoven web having a hydrohead value as measured by Method 5514 of Federal Test Method Standard No. 191A which is at least 50 percent of the hydrohead value of the coated nonwoven web before exposure to the oxidizing gas plasma. The antistatic agent and the nonwoven web are as described hereinbefore.

DETAILED DESCRIPTION OF THE INVENTION

Figure 1:
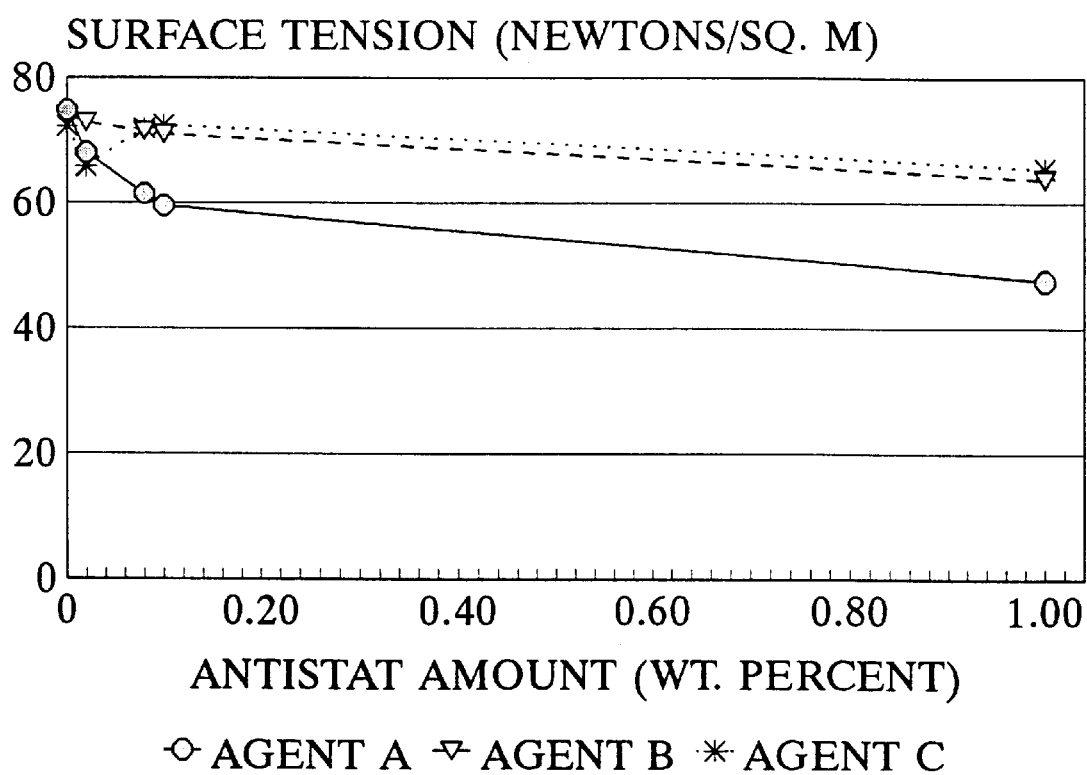
FIG. 1 is a plot of the surface tension of water, in $10^{-3}$ Newtons per meter, which contains various amounts of each of three antistatic agents, two of which are antistatic agents of the present invention.

As used herein, the term "antistatic agent" refers to a material or a mixture of two or more materials which, when applied to the surfaces of the fibers of which a nonwoven web is composed, aid in the dissipation of static charges from the surfaces of the fibers. Thus, an antistatic agent increases the electrical conductivity of the fibers, and, as a consequence, the electrical conductivity of the nonwoven web.

As used herein, the term "coating" refers to the coating of the surfaces of fibers or films with the antistatic agent, and/or locating the antistatic agent at fiber-fiber interstices and/or bond points. The coating of all of the fibers of which a nonwoven web is composed is not necessarily required for all applications. In order to impart antistatic characteristics to a nonwoven web, it may be sufficient to coat only those fibers which constitute a surface of the web.

The term "alkali metal" as used herein means the metals of Group 1a of the Periodic Table of the Elements, e.g., lithium, sodium, potassium, rubidium, and cesium, with the first three metals of the series having the most practical utility.

The term "hydrohead value" is the value obtained in accordance with Method 5514 of Federal Test Method Standard No. 191A. The hydrohead value is reported herein as Newtons per square meter.

As used herein, "surface resistivity" means the surface resistivity as determined in accordance with MTCC Test Method 76:1972 (see also U.S. Pat. No. 4,041,203, infra). Such resistivity is reported as ohms per square inch or simply ohms per square. The test utilizes a Model 610C Electrometer (Keithley Instruments Inc., Cleveland, Ohio 44139) and a Model 240A high DC voltage supply (Keithley Instruments Inc.). Test samples are equilibrated at 23° C. and 50 percent relative humidity for 24 hours.

The terms "phosphate," "phosphate ester," "alkyl phosphate," and similar terms, in both the singular and the plural, refer to alkyl esters of orthophosphoric acid (commonly called phosphoric acid), $H_3PO_4$. Because phosphoric acid is a tribasic $P^V$ acid, mono-, di-, and triesters are possible. The mono- and diesters may exist in either acid or salt form. In fact, diesters are strongly acidic and are completely in the anionic (ionized) form at normal pH values.

As used herein in relation to one or more layers of sterilization wrap surrounding items to be sterilized or a container in which such items are located, the term "sealing relationship" means that each layer is taped or otherwise closed or sealed in order to preserve the barrier properties of each layer.

The term "nonwoven web" is used herein to mean a web having a structure of individual fibers which are interlaid in a generally random manner, not in an identifiable manner as in a knitted fabric, and is intended to include any nonwoven web. For example, the term includes those prepared by the well-known melt-extrusion processes as meltblowing, coforming, and spunbonding. Such processes are exemplified by the following references, each of which is incorporated herein by reference:

(a) meltblowing references include, by way of example, U.S. Patent No. 3,016,599 to R. W. Perry, Jr., U.S. Pat. No. 3,704,198 to J. S. Prentice, U.S. Pat. No. 3,755,527 to J. P. Keller et al., U.S. Pat. No. 3,849,241 to R. R. Butin et al., U.S. Pat. No. 3,978,185 to R. R. Butin et al., and U.S. Pat. No. 4,663,220 to T. J. Wisneski et al. See, also, V. A. Wente, "Superfine Thermoplastic Fibers", *Industrial and Engineering Chemistry*, Vol. 48, No. 8, pp. 1342–1346 (1956); V. A. Wente et al., "Manufacture of Superfine Organic Fibers", Navy Research Laboratory, Washington, D.C., NRL Report 4364 (111437), dated May 25, 1954, United States Department of Commerce, Office of Technical Services; and Robert R. Butin and Dwight T. Lohkamp, "Melt Blowing—A One-Step Web Process for New Nonwoven Products", *Journal of the Technical Association of the Pulp and PaDer Industry*, Vol. 56, No.4, pp. 74–77 (1973);

(b) coforming references (i.e., references disclosing a meltblowing process in which fibers or particles are commingled with the meltblown fibers as they are formed) include U.S. Pat. No. 4,100,324 to R. A. Anderson et al. and U.S. Pat. No. 4,118,531 to E. R. Hauser; and (c) spunbonding references include, among others, U.S. Pat. No. 3,341,394 to Kinney, U.S. Pat. No. 3,655,862 to Dorschner et al., U.S. Pat. No. 3,692,618 to Dorschner et al., U.S. Pat. No. 3,705,068 to Dobo et al., U.S. Pat. No. 3,802,817 to Matsuki et al., U.S. Pat. No. 3,853,651 to Porte, U.S. Pat. No. 4,064,605 to Akiyama et al., U.S. Pat. No. 4,091,140 to Harmon, U.S. Pat. No. 4,100,319 to Schwartz, U.S. Pat. No. 4,340,563 to Appel and Morman, U.S. Pat. No. 4,405,297 to Appel and Morman, U.S. Pat. No. 4,434,204 to Hartman et al., U.S. Pat. No. 4,627,811 to Greiser and Wagner, and U.S. Pat. No. 4,644,045 to Fowells.

Other methods for preparing nonwoven webs are known and may be employed. For example, the term also includes nonwoven webs prepared from relatively short fibers to form a web or sheet. Methods employed to prepare such webs include air laying, wet laying, carding, and the like. In some cases, it may be either desirable or necessary to stabilize the nonwoven web by known means, such as thermal pattern bonding (i.e., pattern bonding by the application of heat and pressure), through-air bonding, and hydroentangling.

The phrase "pattern bonding by the application of heat and pressure" means any process by which a nonwoven web is passed through a nip formed by a pair of opposed rolls. Either or both rolls may have a regular or irregular surface pattern of continuous lands and grooves or isolated (discontinuous) projections. For example, the nonwoven web may be pattern bonded by the application of heat and pressure in the ranges of from about 80° C. to about 180° C. and from about 150 to about 1,000 pounds per linear inch (from about 59 kg/cm to about 178 kg/cm), respectively, employing a pattern with from about 10 to about 1,000 bond regions/inch$^2$ (from about 1 to about 155 bond regions/cm$^2$) covering from about 5 to about 50 percent of the web surface area. Representative of known pattern bonding procedures are, by way of example only, U. S. Design Pat. No. 239,566 to Vogt, U.S. Design Pat. No. 264,512 to Rogers, U.S. Pat. No. 3,855,046 to Hansen et al., and U.S. Pat. No. 4,493,868 to Meitner.

The term "synthetic polymer fibers" is used herein to mean fibers composed of any synthetic, usually thermoplastic, polymer which may be used to prepare nonwoven webs. Examples of thermoplastic synthetic polymers include, by way of illustration only, end-capped polyacetals, such as poly(oxymethylene) or polyfornmaldehyde, poly(tri-chloroacetaldehyde), poly(n-valeraldehyde), poly(acetaldehyde), and poly(propionaldehyde); acrylic polymers, such as polyacrylamide, poly(acrylic acid), poly(methacrylic acid), poly(ethyl acrylate), and poly(methyl methacrylate); fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoro-ethylene copolymers, poly(vinylidene fluoride), and poly(vinyl fluoride); polyamides, such as poly(6-aminocaproic acid) or poly($\epsilon$-caprolactam), poly(hexamethylene adipamide), poly(hexamethylene sebacamide), and poly(1 1-amino-undecanoic acid); polyaramides, such as poly(imino-1,3-phenylene-iminoisophthaloyl) or poly(m-phenylene isophthal-amide); parylenes, such as poly-p-xylylene and poly-(chloro-pxylylene); polyaryl ethers, such as poly(oxy-2,6-dimethyl-1,4-phenylene) or poly(p-phenylene oxide); polyaryl sulfones, such as poly(oxy-1,4-phenylenesulfonyl-1,4-phenyleneoxy-1,4-phenylene-iso-propylidene-1,4-phenylene) and poly(sulfonyl-1,4-phenyleneoxy-1,4-phenylenesulfonyl-4,4-biphenylene), and the like; polycarbonates, such as poly(bisphenol A) carbonate or poly(carbonyldioxy-1,4-phenyleneiso-propylidene-1,4-phenylene); poly-esters, such as poly(ethylene terephthalate), poly(tetramethylene terephthalate) and poly(cyclohexylene-1,4-dimethylene terephthalate) or poly(oxymethylene-1,4-cyclohexyl-enemethyleneoxy-terephthaloyl); poly-aryl sulfides, such as poly(p-phenylene sulfide) or poly(thio-1,4-phenylene); polyimides, such as poly(pyromellitimido-1,4-phenylene); polyolefins, such as polyethylene, polypropylene, poly(1-butene), poly(2-butene), poly(1-pentene), poly(2-pentene), poly(3-methyl-1-pentene), and poly(4-methyl-1-pentene); vinyl polymers, such as poly(vinyl acetate), poly(vinylidene chloride), and poly(vinyl chloride); diene polymers, such as 1,2-poly-1,3-butadiene, 1,4-poly-1,3-butadiene, polyisoprene, and polychloro-prene; polystyrenes; and copolymers of the foregoing, such as acrylonitrile-butadiene-styrene (ABS) copolymers.

Desirably, the nonwoven web will be prepared from a synthetic polyolefin. In general, the term "thermoplastic polyolefin" is used herein to mean any thermoplastic polyolefin which can be used for the preparation of nonwoven webs. Examples of thermoplastic polyolefins include polyethylene, polypropylene, poly(1-butene), poly(2- butene), poly(1-pentene), poly(2-pentene), poly(3-methyl-1-pentene), poly(4-methyl-1-pentene), and the like. In addition, such term is meant to include blends of two or more polyolefins and random and block copolymers prepared from two or more different un-saturated monomers. Because of their commercial importance, the more desired polyolefins are polyethylene and polypropylene.

As stated earlier, the method of the present invention includes providing a nonwoven web; coating the nonwoven web with from about 0.005 to about 3 percent by weight, based on the weight of the web, of an antistatic agent; and exposing the coated nonwoven web to an oxidizing gas plasma. The antistatic agent is adapted to be free of malodors after exposure of the coated nonwoven web. The antistatic agent may be further adapted to provide a sterilized nonwoven web having a hydrohead value as measured by Method 5514 of Federal Test Method Standard No. 191A which is at least 50 percent of the hydrohead value of the coated nonwoven web before exposure to the oxidizing gas plasma. The antistatic agent also may be adapted to provide a sterilized nonwoven web having a surface resistivity in ohms which is lower than the surface resistivity in ohms of the coated nonwoven web before exposure of the coated nonwoven web to the oxidizing gas plasma.

The antistatic agents of the present invention are best exemplified by two types of compounds. The first type includes alkali metal or ammonium salts of mono- and di-$C_3$-alkyl phosphates in which the $C_3$-alkyl moiety is an alkyl group containing three carbon atoms optionally substituted with hydroxy groups. Stated differently, the first group is composed of mono- and diesters of phosphoric acid with alcohols, diols, and triols containing three carbon atoms. Examples of such alcohols, diols, and triols include propyl alcohol (or n-propyl alcohol), isopropyl alcohol (or 2-hydroxypropane), propylene glycol (or 1,2-dihydroxypropane), trimethylene glycol (or 1,3-dihydroxypropane), and glycerol (or 1,2,3-trihydroxypropane). Accordingly, the ester portions of the first type of antistatic agents are propyl or isopropyl (i.e., 2-propyl) groups, optionally substituted with one or two hydroxy groups. More particularly, the antistatic agents of the present invention include the alkali metal or ammonium salts of a propyl ester of phosphoric acid, or propyl phosphate; a dipropyl ester of phosphoric acid, or dipropyl phosphate; an isopropyl ester of phosphoric acid, or isopropyl phosphate; a diisopropyl ester of phosphoric acid, or diisopropyl phosphate; a 2-hydroxypropyl ester of phosphoric acid, or 2-hydroxypropyl phosphate; a di(2-hydroxypropyl) ester of phosphoric acid, or di(2-hydroxypropyl) phosphate; a 1- hydroxy-2-propyl ester of phosphoric acid, or 1-hydroxy-2-propyl phosphate; a di(1-hydroxy-2-propyl) ester of phosphoric acid, or di(1-hydroxy-2-propyl) phosphate; a 3-hydroxypropyl ester of phosphoric acid, or 3-hydroxypropyl phosphate; a di(3-hydroxypropyl) ester of phosphoric acid, or di(3-hydroxypropyl) phosphate; a 2,3-dihydroxypropyl ester of phosphoric acid, or 2,3-dihydroxypropyl phosphate; a bis(2,3-dihydroxypropyl) ester of phosphoric acid, or bis(2,3-dihydroxypropyl) phosphate; a bs,3-dihydroxy-2-propyl ester of phosphoric acid, or 1,3-dihydroxy-2-propyl phosphate; a bis(1,3-dihydroxy-2-propyl) ester of phosphoric acid, or bis(1,3-dihydroxy-2-propyl) phosphate; and mixtures of two or more of the foregoing.

By way of example, the antistatic agent may be a mixture of alkali metal or ammonium salts of propyl phosphate and dipropyl phosphate. For example, the salts may be potassium salts. Also by way of example, the antistatic agent may be a mixture of alkali metal or ammonium salts of isopropyl phosphate and diisopropyl phosphate. Again by way of example, the salts may be potassium salts.

The second type of compounds which exemplify the antistatic agents of the present invention include alkali metal or ammonium salts of ,carbon substituted alkyl phosphates, di(βcarbon substituted alkyl) phosphates, or mixtures of two or more of the foregoing. The βcarbon substituted alkyl group in general may contain from four to about seven carbon atoms. The term ",carbon" refers, in accordance with common practice, to the carbon atom immediately adjacent to the carbon atom which is covalently bonded to a phosphate oxygen atom. The βcarbon may have either one or two substitutents. As used herein, the term "substituent" means an atom other than hydrogen which is effective in minimizing or preventing malodor when the antistatic agent is present on a web or sterilization wrap which is sterilized in an oxidizing gas plasma. Examples of suitable substituents include, without limitation, such groups as methyl and ethyl; hydroxymethyl; and the like.

Examples of phosphates encompassed by the second type of compounds include, by way of illustration only, alkali metal or ammonium salts of an isobutyl ester of phosphoric acid, or isobutyl phosphate; a diisobutyl ester of phosphoric acid, or diisobutyl phosphate; pentaerythritol mono- and diesters of phosphoric acid, or 3-hydroxy-2,2-bis(hydroxymethyl)propyl phosphate and bis[3-hydroxy-2,2-bis(hydroxy-methyl)propyl] phosphate; 2-methyl-I-butyl phosphate; di(2-methyl-I-butyl) phosphate; 2,2-dimethyl-1-butyl phosphate; bis(2,2-dimethyl-1-butyl) phosphate; 2,3-dimethyl-1-butyl phosphate; bis(2,3-dimethyl-l-butyl) phosphate; 2-ethyl-I-butyl phosphate; di(2-ethyl-1-butyl) phosphate; 2-methyl-1-pentyl phosphate; di(2-methyl-1-pentyl) phosphate; 2,2-dimethyl-1-pentyl phosphate; bis(2,2-dimethyl-1-pentyl) phosphate; 2,3-dimethyl-1-pentyl phosphate; bis(2,3-dimethyl-1-pentyl) phosphate; and the like; and mixtures of two or more of the foregoing.

By way of example, the antistatic agent may be a mixture of the alkali metal or ammonium salts of isobutyl phosphate and diisobutyl phosphate. By way of example, the salts may be potassium salts.

In general, the nonwoven web may be any nonwoven web substantially composed of synthetic polymer fibers. For example, the nonwoven web may be a meltblown web. As another example, the meltblown web may be a component of a laminate. For example, the nonwoven web may include a first layer which is a nonwoven web composed of synthetic polymer fibers and a second layer, adjacent to the first layer in laminar surface-to-surface relationship, which is a nonwoven web composed of synthetic polymer fibers. As another example, the nonwoven web may include a first layer having a first side and a second side, a second layer adjacent to the first side of the first layer in laminar surface-to-surface relationship, and a third layer adjacent to the second side of the first layer in laminar surface-to-surface relationship. Each nonwoven web typically will be substantially composed of synthetic polymer fibers. For example, the synthetic polymer fibers of which the first, second, and third layers are composed may be polyolefin fibers. For example, the polyolefin fibers may be polyethylene fibers, polypropylene fibers, or a combination thereof. The first layer may be a meltblown web and each of the second and third layers may be a spunbonded web. The laminate or any layer of combination of layers may be pattern bonded by the application of heat and pressure. Laminates also include one or more nonwoven web layers with one or more film layers.

The two-layered and three-layered laminates described above are known in the art and often are referred to as SM and SMS fabrics, respectively. See, for example, U.S. Pat. No. 4,041,203 to Brock et al., which patent is incorporated herein by reference in its entirety.

Coating in general may be accomplished by any means known to those having ordinary skill in the art. By way of example, such means include, but are not limited to, dipping and nipping, doctor blading, brushing, spraying, and direct and offset gravure printing or coating.

The present invention further provides a fibrous sheet-like material which includes a gas-permeable, water-impermeable nonwoven web coated with from about 0.005 to about 3 percent by weight, based on the weight of the web, of an antistatic agent. The antistatic agent is adapted, after exposure of the coated water-impermeable nonwoven web to an oxidizing gas plasma, to be free of malodors and to have a hydrohead value as measured by Method 5514 of Federal Test Method Standard No. 191A which is at least 50 percent of the hydrohead value of the coated water-impermeable nonwoven web before exposure to the oxidizing gas plasma. The antistatic agent in general may be that described hereinbefore. The sterilization wrap may be a nonwoven web or a laminate, also as described hereinbefore.

The present invention additionally provides a barrier fabric, a sterilization wrap, and a surgical garment, each composed of the fibrous sheet-like material described hereinabove.

The present invention still further provides a medical procedure pack which includes one or more items to be sterilized and one or more layers of sterilization wrap surrounding the one or more items to be sterilized in a sealing relationship. The medical procedure pack may further include a fluid permeable container having an exterior and an interior, with the one or more items to be sterilized being present in the interior of the container. The sterilization wrap includes a gas-permeable, water-impermeable nonwoven web coated with from about 0.005 to about 3 percent by weight, based on the weight of the web, of an antistatic agent, wherein the antistatic agent is adapted, after exposure of the coated water-impermeable nonwoven web to an oxidizing gas plasma, to be free of a malodor and to provide a nonwoven web having a hydrohead value as measured by Method 5514 of Federal Test Method Standard No. 191A after exposure to the oxidizing gas plasma which is at least 50 percent of the hydrohead value of the coated water-impermeable nonwoven web before exposure to the oxidizing gas plasma. The antistatic agent may be further adapted to have a surface resistivity in ohms which is lower than the surface resistivity in ohms of the coated water-impermeable nonwoven web before exposure to the oxidizing gas plasma. The antistatic agent and the nonwoven web are as described hereinbefore.

In a variation of the medical procedure pack described above, a container having an exterior and an interior may have one or more items to be sterilized present in the interior of the container, in which at least a portion of the container comprises the gas-permeable, water-impermeable nonwoven web described earlier. Such container often is referred to in the art as a peel pouch, one side of which is the foregoing nonwoven web. The container typically contains a single item to be sterilized.

Finally, the present invention provides a method of manufacturing a nonwoven web adapted to be sterilized by exposure to an oxidizing gas plasma. The method involves providing a nonwoven web and coating the nonwoven web with from about 0.005 to about 3 percent by weight, based on the weight of the web, of an antistatic agent. The antistatic agent is adapted to be free of a malodor after exposure of the coated nonwoven web to the oxidizing gas plasma. The antistatic agent may be further adapted to provide a sterilized nonwoven web having a hydrohead value as measured by Method 5514 of Federal Test Method Standard No. 191A which is at least 50 percent of the hydrohead value of the coated nonwoven web before exposure to the oxidizing gas plasma. The antistatic agent and the nonwoven web are as described hereinbefore.

The present invention is further described by the examples which follow. Such examples, however, are not to be construed as limiting in any way either the spirit or the scope of the present invention.

EXAMPLE 1

A thermally bonded laminate of a spunbond-meltblown-spunbond (SMS) fabric was prepared essentially as described in U.S. Pat. No. 4,041,203, infra. The SMS fabric had a basis weight of 48 grams per square meter or gsm. The SMS fabric was treated with antistatic agents by the dip and squeeze method described in U.S. Pat. No. 4,041,203. Three different antistatic agents were used: (1) Antistatic Agent A, which was supplied as an approximately 50 percent by weight solution of dipotassium butyl phosphate and potassium dibutyl phosphate in approximately equimolar amounts (Zelec KC, Du Pont Chemicals, Wilmington, Del. 19898); (2) Antistatic Agent B, which was supplied as an approximately 50 percent by weight solution of dipotassium propyl phosphate and potassium dipropyl phosphate in approximately equimolar amounts (Du Pont Chemicals); and (3) Antistatic Agent C, which was supplied as an approximately 50 percent by weight solution of dipotassium isopropyl phosphate and potassium diisopropyl phosphate in approximately equimolar amounts (Du Pont Chemicals)

Two levels of each of Antistatic Agents A and B were applied to the fabric: (1) 0.1 percent by weight, and (2) 0.3 percent by weight. For a target level of 0.1 percent by weight of antistatic agent on the fabric, the treatment solution was obtained by diluting the solution as supplied with hexanol and deionized water to give a concentration of antistatic agent and hexanol in the treatment solution of 0.22 percent by weight and 0.55 percent by weight, respectively. The second target level of 0.3 percent by weight was obtained in a similar manner, except that the final concentrations of antistatic agent and hexanol were 0.67 percent by weight and 0.55 percent by weight, respectively. Antistatic Agent C was applied at a target level of 0.2 percent by weight, with the concentrations of antistatic agent and hexanol in the treatment solution being 0.20 percent by weight and 0.55 percent by weight, respectively. In each case, the working volume was 8 liters.

Each antistatic agent was topically applied to the fabric by passing the fabric at a speed of 40 feet per minute (about 20 centimeters per second) into the treatment solution and through a nip set at a pressure of 60 psi. The wet fabric then was dried by passing it sequentially over a series of six steam cans set at a temperature of about 113° C. A sample of fabric was removed immediately after the nip in order to measure wet pickup on the fabric and calculate the percent add-on level of the antistatic agent on a dry weight basis.

The antistatic properties of the treated fabrics were determined by the surface resistivity test. Five replicates were measured and an average value calculated. The effectiveness of the fabrics as a barrier to liquids was determined by the hydrohead test already described. Five replicates of this test also were taken and averaged. The treated fabrics are summarized in Table 1 and the results are summarized in Table 2; in Table 1, the three antistatic agents are represented by the letters A, B, and C.

TABLE 1

Summary of Treated Fabrics

| | Treatment | |
|---|---|---|
| Sample | Add-on[a] | Antistatic Agent |
| 1-1 | None | None |
| 1-2 | 0.11 | A |
| 1-3 | 0.35 | A |
| 1-4 | 0.11 | B |
| 1-5 | 0.34 | B |
| 1-6 | 0.20 | C |

[a]Add-on as percent by weight, based fabric weight.

TABLE 2

Surface Resistivity and Hydrohead Data

| | | Surface Resistivity | | |
|---|---|---|---|---|
| Sample | Age[a] | Ratio[b] | Value[c] | Hydrohead[d] |
| 1-1 | 7 | 0/5 | >$10^{14}$ | 5070 |
|  | 14 | 0/5 | >$10^{14}$ | — |
| 1-2 | 7 | 0/5 | >$10^{14}$ | 4770 |
|  | 14 | 5/5 | $10^8$ | — |
| 1-3 | 7 | 3/5 | $10^8$ | 1930 |
|  | 14 | 5/5 | $10^8$ | — |
| 1-4 | 7 | 3/5 | $10^{12}$ | 5250 |
|  | 14 | 0/5 | >$10^{14}$ | — |
| 1-5 | 7 | 4/5 | $10^{10}$ | 3950 |
|  | 14 | 5/5 | $10^{10}$ | — |
| 1-6 | 7 | 5/5 | $10^{12}$ | 5200 |

[a]Age of the sample at the time of testing, in days.
[b]Pass ratio, the number of samples passing/number of samples tested. Samples were considered to have passed when the surface resistivity was less than $10^{14}$ ohms. Values of less than $10^{14}$ ohms represent the average surface resistivity of samples which passed.
[c]In ohms per square inch (to convert to ohms per $cm^2$, divide by 6.45).
[d]In Newtons per square meter.

Upon comparing the data in Table 2 for samples 1–2 through 1–6 to the data for sample 1–1, it is seen that both Antistatic Agents B and C provide acceptable surface resistivity properties with significantly less reduction of the hydrohead values, unlike Antistatic Agent A.

EXAMPLE 2

Several of the various fabrics produced in Example 1 were sterilized by an oxidizing gas plasma substantially in accordance with U.S. Pat. No. 4,643,876 to Jacobs et al., which patent is incorporated herein by reference in its entirety. Such sterilization employed a hydrogen peroxide plasma and a STERRAD™ 100 Sterilization System (Advanced Sterilization Products, Irvine, California 92718); the manufacturer's recommended procedures were followed.

Gas chromatography/mass spectrometry (GC/MS) was used to analyze fabrics for odoriferous chemicals. Samples 1–1, 1–3, and 1–5 from Example 1 (Table 1) were analyzed before and after exposure to the STERRAD™ gas plasma. During the GC/MS analysis, about 5 grams of fabric was placed in a 100 ml sparging tube and 5 purged with a stream of helium at room temperature for 15 minutes. The purged volatile chemicals were identified by the GC/MS technique in accordance with known and accepted procedures. Table 3 shows a summary of the results.

TABLE 3

Summary of GC/MS Data

| Sample[a] | Description | Summary of GC/MS Data |
|---|---|---|
| 1-1 | No antistatic agent treatment and not sterilized. | No volatile chemicals were detected. |
| 1-1 | No antistatic agent and STERRAD ™ sterilized. | No volatile chemicals were detected. |
| 1-3 | 0.35 Percent by weight Antistatic Agent A and not sterilized. | In a first trial, small amounts of acetone, hexane, methyl vinyl ketone, and 1-butanol were detected. In a second trial, small amounts of acetaldehyde, acetone, dichloromethane, 1-butanol, and silicone were detected. Chloroform was represented by the largest peak. The presence of methyl vinyl ketone was questionable. |
| 1-3 | 0.35 Percent by weight Antistatic Agent A and STERRAD ™ sterilized. | In a first trial, small amounts of acetone, hexane, and 1-butanol were detected. There was very large methyl vinyl ketone peak. In a second trial, small amounts of acetaldehyde, acetone, dichloromethane, 1-butanol, and silicone were detected. Chloroform was represented by a moderate peak. The largest peak represented methyl vinyl ketone. |
| 1-5 | 0.34 Percent by weight Antistatic Agent B and not sterilized. | Small amounts of acetaldehyde, 2-propanol, acetone, dichloromethane, chloroform, silicone, and toluene were detected. No methyl vinyl ketone was found. |
| 1-5 | 0.34 Percent by weight Antistatic Agent B and STERRAD ™ sterilized. | Small amounts of acetaldehyde, 2-propanol, acetone, dichloromethane, and chloroform were found. Silicone was represented by a moderate and most intense peak. No methyl vinyl ketone was detected. |

[a]Sample number designations are from Table 1.

The data in Table 3 strongly suggest that methyl vinyl ketone, a chemical with a strong pungent odor (Merck Index), is responsible for the unpleasant odor that was observed when fabric treated with Antistatic Agent A was exposed to an oxidizing gas plasma (e.g., the STERRAD™ sterilization procedure).

It may be noted that the observation of an odor associated with the oxidizing gas plasma sterilization of fabric to which Antistatic Agent A had been applied may be concentration dependent. For example, when a commercially available sterilization wrap to which Antistatic Agent A had been applied at a level of 0.025 percent by weight (KIMGUARD® ULTRA™, Kimberly-Clark Corporation, Roswell, Ga. 30076) was sterilized by the STERRAD™ procedure, no volatile chemicals were detected.

EXAMPLE 3

Surface tension data were collected in an effort to explain the unexpected hydrohead results obtained with the use of Antistatic Agents B and C. The surface tension of water with various amounts of added Antistatic Agent A, B, or C was measured with a Fisher Surface Tensiometer 20 using a platinum-iridium du Nouy ring (Fisher Scientific Company, Pittsburgh, Pa.). For these measurements, about 80 ml of distilled, deionized water was placed in a 100 ml Pyrex beaker. After an initial surface tension measurement was taken, a drop of the antistatic agent solution was added to the water and the resulting solution was stirred for about 5 minutes. The surface tension of the new solution then was measured, and the procedure was repeated until completed. Table 4 summarizes the surface tension data for Antistatic Agents A, B, and C.

TABLE 4

Summary of Surface Tension Data

| Antistatic Agent | Amount in Water[a] | Surface Tension[b] |
|---|---|---|
| A | 0 | 74.8 |
|   | 0.015 | 67.9 |
|   | 0.067 | 61.4 |
|   | 0.109 | 59.5 |
|   | 1.007 | 47.6 |
| B | 0 | 74 |
|   | 0.024 | 72.8 |
|   | 0.078 | 71.4 |
|   | 0.112 | 70.9 |
|   | 1.112 | 63.2 |
| C | 0 | 72.2 |
|   | 0.028 | 65.8 |
|   | 0.075 | 71.8 |
|   | 0.104 | 72.4 |
|   | 0.990 | 65.6 |

[a]Percent by weight.
[b]In $10^{-3}$ Newtons per meter.

In order to better illustrate the effects of the antistatic agents on the surface tension of water, the data in Table 4 were plotted as line graphs, shown in FIG. 1. It can be seen from the surface tension data of Table 4 and FIG. 1 that Antistatic Agents B and C unexpectedly depress the water surface tension much less than does Antistatic Agent A. Thus, Antistatic Agents B and C are less surface active antistatic treatments compared to Antistatic Agent A.

EXAMPLE 4

The fabrics treated with a target level of 0.1 percent by weight Antistatic Agents A and B (Samples 1–2 and 1–4, respectively), described in Example 1 (Table 1), were evaluated by the hydrohead and surface resistivity tests after exposure to the STERRAD™ oxidizing gas plasma treatment. Each fabric was cut into four pieces about 12 inches (about 30 cm) in the cross direction and about 15 inches (about 38 cm) in the machine direction. Each piece was placed in the STERRAD™ chamber in a different location, i.e., top front (TF), top back (TB), lower front (LF), and lower back (LB). The pieces were removed after the STERRAD™ treatment and tested for hydrohead (two samples of each fabric) and surface resistivity (five samples of each fabric) as described in Example 1. The data are summarized in Tables 5 and 6.

TABLE 5

Hydrohead Data

| Sample | Antistatic Agent | Hydrohead[a]/Location in Chamber | | | | |
|---|---|---|---|---|---|---|
|   |   | NT | TF | TB | LF | LB |
| 4-1 | A | 5180 | 950 | 1200 | 780 | 680 |
| 4-2 | B | 5800 | 4350 | 3850 | 1080 | 2980 |

[a]In Newtons per square meter.

TABLE 6

Surface Resistivity Data

| Sample | Antistatic Agent | Surface Resistivity[a]/Location in Chamber | | | | |
|---|---|---|---|---|---|---|
|   |   | NT | TF | TB | LF | LB |
| 4-1 | A | $10^8$ | $10^{13}$ | $10^{13}$ | $10^{10}$ | $10^{11}$ |
| 4-2 | B | $>10^{14}$ | $10^{11}$ | $10^{12}$ | $10^9$ | $10^{10}$ |

[a]In ohms per square inch (to convert to ohms per cm$^2$, divide by 6.45).

Figure 2:
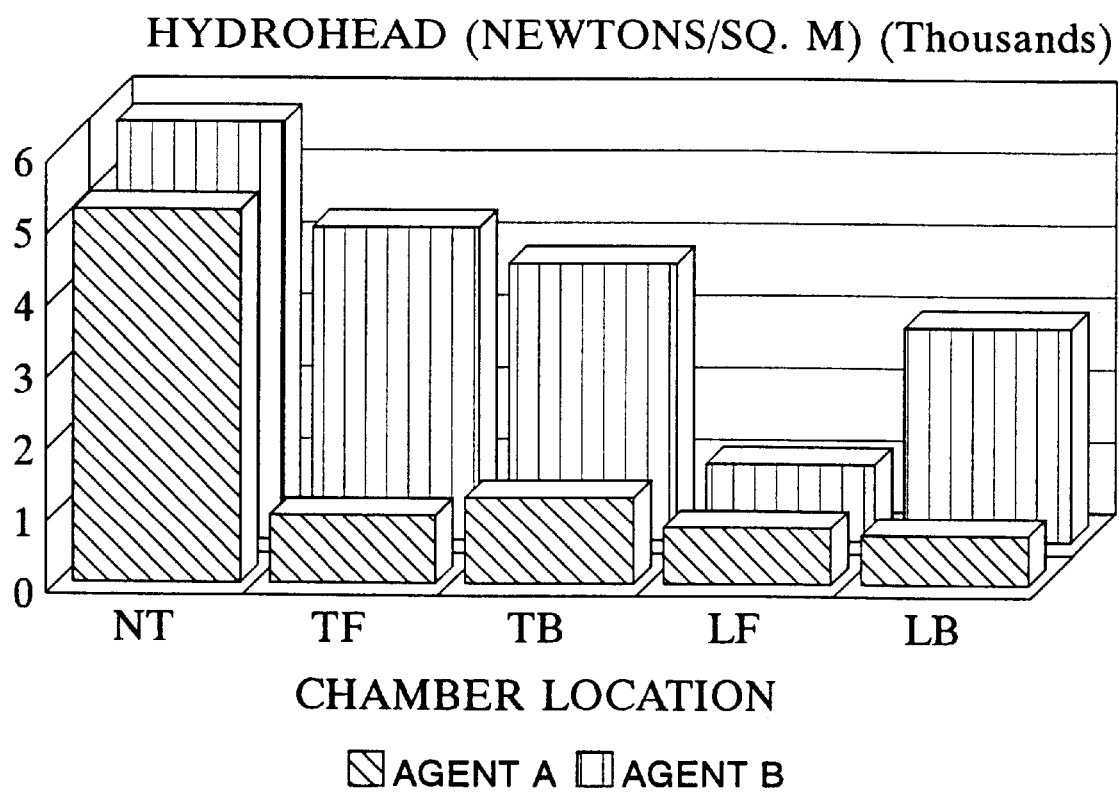
FIG. 2 is a plot of the hydrohead values, in Newtons per square meter, of nonwoven fabrics treated with either of the two antistatic agents employed in FIG. 1 and sterilized with an oxidizing gas plasma in accordance with the present invention, versus the location of the fabric in the sterilization chamber.
Figure 3:
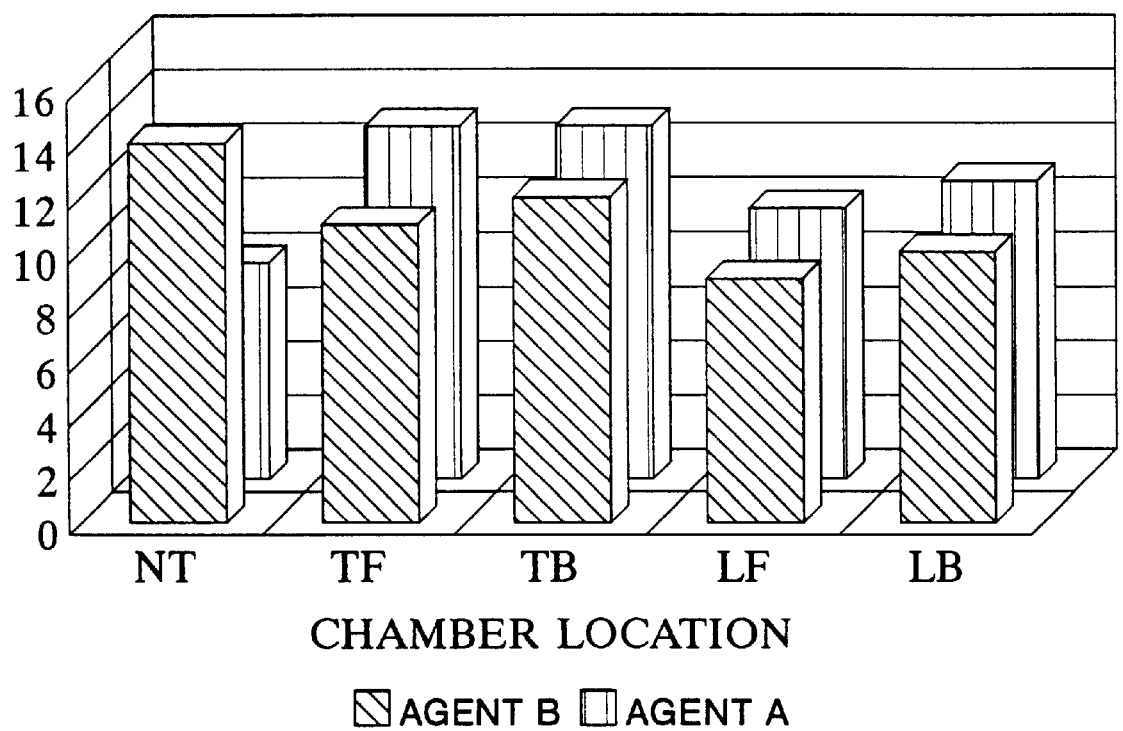
FIG. 3 is a plot of the surface resistivity values, in ohms per square inch (ohms per 6.45 square centimeters or $cm^2$) of nonwoven fabrics treated with either of the two antistatic agents employed in FIG. 1 and sterilized with an oxidizing gas plasma in accordance with the present invention, versus the location of the fabric in the sterilization chamber.

In order to better illustrate the effect of location within the sterilization chamber and differences between the two antistatic agents studied, the data in Tables 5 and 6 were plotted as line graphs, shown in FIGS. 2 and 3, respectively. Tables 5 and 6 and FIGS. 2 and 3 suggest the following conclusions:

Before Sterilization

Fabric treated with Antistatic Agent A had a surface resistivity which was well below the fail limit of $10^{14}$ ohms per square inch.

Fabric treated with Antistatic Agent B had a surface resistivity which was slightly above the fail limit.

Fabric treated with Antistatic Agent B had a higher hydrohead value than fabric treated with Antistatic Agent A.

After Sterilization

Fabric treated with Antistatic Agent B had lower surface resistivities than fabric treated with Antistatic Agent A, regardless of the location of the fabric in the sterilization chamber.

Fabric treated with Antistatic Agent B had higher hydrohead values than fabric treated with Antistatic Agent A, regardless of the location of the fabric in the sterilization chamber.

The hydrohead values for fabric treated with Antistatic Agent A were only about 15–20 percent of the hydrohead value for fabric which had not been sterilized.

The hydrohead values for fabric treated with Antistatic Agent B typically were greater than about 50 percent of the hydrohead value for fabric which had not been sterilized.

Apparently anomalous results were associated with the lower front of the sterilization chamber, for reasons as yet unknown.

EXAMPLE 5

The procedure of Example 1 was repeated with additional antistatic agents and levels of antistatic agents on the fabric. The antistatic agents employed were as follows: (1) Antistatic Agent A of Example 1; (2) Antistatic Agent D, which was supplied as an approximately 50 percent by weight solution of dipotassium isobutyl phosphate and potassium diisobutyl phosphate in approximately equimolar amounts (polyfix™ N, Schill+Seilacher GmbH & Co., Boblingen, Germany); (3) Antistatic Agent E, which was supplied as an approximately 50 percent by weight solution of the dipotassium salt of a propylene glycol ester of phosphoric acid and the potassium salt of a propylene glycol diester of phosphoric acid in approximately equimolar amounts (Quadrastat™ PPG-50, Manufacturers Chemical, Cleveland, Tennessee); and (4) Antistatic Agent F, which was supplied as an approximately 50 percent by weight solution of the dipotassium salt of a pentaerythritol ester of phosphoric acid and the potassium salt of a pentaerythritol diester of phosphoric acid in a molar ratio of approximately 1:3 (Quadrastat™ P4K, Manufacturers Chemical, Cleveland, Tennessee). Most, if not all, of the antistatic agents are known to also include minor amounts (e.g., up to about 20 mole percent) of the pyrophosphate, as well as small amounts of the triester and phosphoric acid. It may be noted that the pyrophosphate, an example of a chain or polyphosphate, contains two phosphorus atoms linked by an oxygen bridge. The pyrophosphate typically also contains two ester groups; thus, while not as effective an antistatic agent as a phosphoric acid diester, the pyrophosphate is a diester coming within the scope of the present invention. For a discussion of phosphates and pyrophosphates, see F. Albert Cotton, and Geoffrey Wilkinson, "Advanced Inorganic Chemistry: A Comprehensive Text," Fourth Edition, John Wiley & Sons, New York, 1980, pp. 472–6.

Two levels of each antistatic agent were applied to the fabric: (1) 0.01 percent by weight, and (2) 0.08 percent by weight. For a target level of 0.01 percent by weight of antistatic agent on the fabric, the treatment solution was obtained by diluting the solution as supplied with hexanol and deionized water to give a concentration of antistatic agent and hexanol in the treatment solution of 0.017 percent by weight and 0.55 percent by weight, respectively. The second target level of 0.08 percent by weight was obtained in a similar manner, except that the final concentrations of antistatic agent and hexanol were 0.133 percent by weight and 0.55 percent by weight, respectively. In each case, the working volume was 8 liters. Each antistatic agent was topically applied to the fabric as described in Example 1.

The antistatic properties of the treated fabrics were determined by a static decay or charge dissipation test. Five replicates of treated fabric were measured and an average value calculated. The test conforms to the specifications of INDA Standard Test 40.2–92. It differs from Method 4046, Federal Test Methods Standard No. 101C, in the following ways: (a) the specimen size is 3.5×6 inches (about 9×15 centimeters), rather than 3×5 inches (about 8×13 centimeters); (b) samples were tested as received, without aging; (c) samples were conditioned to, and tested in, an atmosphere maintained at a temperature of 23° C. and a relative humidity of 50 percent but are not placed in a desiccating chamber for 24 hours prior to testing; and (d) five specimens, rather than three, were tested for each sample. See also the National Fire Prevention Association (NFPA) Standard 99-1986. It may be noted that the NFPA procedure is identical to the Federal Method, except that NFPA specifies that, prior to testing, specimens should be conditioned for 25 hours or until equilibrium is reached. The test utilized a calibrated static decay meter, such as Model SDM 406C or 406D (Electro-Tech Systems Inc., Glenside, Pa.). As in Example 1, the effectiveness of the treated fabrics as a barrier to liquids was determined by the hydrohead test described earlier. The treated fabrics are summarized in Table 7. The hydrohead and antistatic data are summarized in Tables 8 and 9, respectively.

TABLE 7

Summary of Treated Fabrics

| Sample | Treatment Add-on[a] | Antistatic Agent |
|---|---|---|
| 5-1 | 0.01 | A |
| 5-2 | 0.08 | A |
| 5-3 | 0.01 | D |
| 5-4 | 0.08 | D |
| 5-5 | 0.01 | E |
| 5-6 | 0.08 | E |

TABLE 7-continued

Summary of Treated Fabrics

| Sample | Treatment Add-on[a] | Antistatic Agent |
|---|---|---|
| 5-7 | 0.01 | F |
| 5-8 | 0.08 | F |

[a]Add-on as percent by weight, based on fabric weight.

TABLE 8

Hydrohead Data

| Sample | Hydrohead[d] |
|---|---|
| 5-1 | 4700 |
| 5-2 | 4620 |
| 5-3 | 5330 |
| 5-4 | 4800 |
| 5-5 | 5130 |
| 5-6 | 5350 |
| 5-7 | 5830 |
| 5-8 | 6070 |

[d]In Newtons per square meter.

TABLE 9

Antistatic Data

| Sample | Residual Charge[a] | Charge Acceptance[a] Positive | Charge Acceptance[a] Negative | 50% Decay[b] Positive | 50% Decay[b] Negative |
|---|---|---|---|---|---|
| 5-1 | 0 | 5,000 | 5,000 | 0.15 | 0.17 |
| 5-2 | 0 | 5,000 | 5,000 | 0.013 | 0.003 |
| 5-3 | 0 | 5,000 | 5,000 | 0.36 | 0.34 |
| 5-4 | 0 | 5,000 | 5,000 | 0.017 | 0.003 |
| 5-5 | −916 | 916 | 2,666 | 0 | 0.007 |
| 5-6 | −750 | 1,083 | 2,500 | 0.007 | 0.013 |
| 5-7 | 2,385 | 2,000 | 1,750 | 0.15 | 0.25 |
| 5-8 | 1,000 | 1,833 | 1,916 | 0.10 | 0.02 |

[a]In volts
[b]In seconds

From Table 2, it is noted that fabric which had not been treated with an antistatic agent had a hydrohead of 5070 Newtons per square meter ($Nm^{-2}$). Even with the low add-ons utilized in this example, it is seen from Table 8 that Antistatic Agent A causes a lowering of the hydrohead, compared to the hydrohead for the untreated fabric. At an add-on of 0.01 percent, Antistatic Agent D appears to have caused an increase in the hydrohead, compared with untreated fabric. At an add-on of 0.08 percent, the lowering of the hydrohead was less than the lowering observed with Antistatic Agent A at both add-on levels studied. The hydrohead results for Antistatic Agents E and F were interesting in that the materials not only appeared to increase hydrohead, but also the increase was directly proportional to the add-on level. The amount of hydrohead increase was significantly higher with Antistatic Agent F than with Antistatic Agent E.

Based on the data in Table 9, the antistatic properties of Antistatic Agents A and D were both similar and acceptable. Overall, the properties of Antistatic Agents E and F were marginally acceptable at the add-on levels studied. If the trends observed upon going to the higher add-on level were maintained at even higher add-on levels, Antistatic Agents E and F may give good results at the higher levels.

Finally, none of the antistatic agents studied produced a malodor upon sterilizing the treated fabrics in an oxidizing gas plasma as described in Example 2.

EXAMPLE 6

The procedure of Example 3 was repeated with Antistatic Agents A, D, E, and F. A fifth antistatic agent, labeled G, also was included. Antistatic Agent G (TLF-8285, DuPont Chemicals, Wilmington, Del.) was supplied as an approximately 50 percent by weight solution of dipotassium octyl phosphate and potassium dioctyl phosphate in approximately equimolar amounts. The results are summarized in Table 10.

TABLE 10

Summary of Surface Tension Data

| Antistatic Agent | Amount in Water[a] | Surface Tension[b] |
|---|---|---|
| A | 0.10 | 51.4 |
|   | 0.23 | 44.3 |
|   | 0.44 | 34.8 |
|   | 0.88 | 37.3 |
| D | 0.10 | 46.3 |
|   | 0.23 | 41 |
|   | 0.44 | 32 |
|   | 0.88 | 38.4 |
| E | 0.10 | 69.3 |
|   | 0.23 | 67 |
|   | 0.44 | 66.8 |
|   | 0.88 | 69.7 |
| F | 0.10 | 54.5 |
|   | 0.23 | 54.9 |
|   | 0.44 | 50.3 |
|   | 0.88 | 60.3 |
| G | 0.10 | 28.4 |
|   | 0.23 | 23.1 |
|   | 0.44 | — |
|   | 0.88 | 22.8 |

[a]Percent by weight.
[b]In $10^{-3}$ Newtons per meter.

The data in Table 10 indicate that all of the antistatic agents appear to lower the surface tension of water below the approximately 724×10$^{-3}$ Newtons per meter 5 for water alone (see Table 4). Antistatic Agent G was exceptional in this respect; because of the effectiveness of the material in lowering surface tension, even at low concentrations, the material was not included in the antistatic studies reported in the preceding example. Such effectiveness suggested the desirability in having no more than about seven carbon atoms in the ester portions of the ,carbon substituted mono- and dialkyl phosphates useful in the present invention. Antistatic Agent D was roughly comparable to Antistatic Agent A with respect to the lowering of the surface tension values, yet did not lower hydrohead as much as did Antistatic Agent A (see Table 8). While Antistatic Agents E and F appeared to have a lowering effect on surface tension, such effect seemed to be independent of the concentration of the agent in solution; this was particularly true for Antistatic Agent E.

While the specification has been described in detail with respect to specific embodiments thereof, it will be appreciated by those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of preparing a sterilized nonwoven web, the method comprising:

providing a nonwoven web;

coating the nonwoven web with from about 0.005 to about 3 percent by weight, based on the weight of the web, of an antistatic agent selected from the group consisting of an alkali metal or ammonium salt of a mono- or di-$C_3$-alkyl phosphate in which the $C_3$-alkyl moiety is an alkyl group containing three carbon atoms at least one of said carbon atoms substituted with an hydroxy group, a mixture of two or more of such salts, an alkali metal or ammonium salt of a β-carbon substituted alkyl phosphate, a di(β-carbon substituted alkyl) phosphate, or a mixture of two or more of the foregoing, wherein the β-carbon substituted alkyl group contains from four to about seven of atoms; and sterilizing the coated nonwoven web by exposing the web to an oxidizing gas plasma;

wherein the sterilized coated nonwoven web is free of a malodor after exposure of the coated nonwoven web to the oxidizing gas plasma.

2. The method of claim 1, in which the sterilized coated nonwoven web has a hydrohead value as measured by Method 5514 of Federal Test Method Standard No. 191A which is at least 50 percent of the hydrohead value of the coated nonwoven web before exposure to the oxidizing gas plasma.

3. The method of claim 1, in which the sterilized coated nonwoven web has a surface resistivity which is lower than the surface resistivity of the coated nonwoven web before exposure of the coated nonwoven web to the oxidizing gas plasma.

4. The method of claim 1, in which the antistatic agent is an alkali metal or ammonium salt of propyl phosphate, dipropyl phosphate, isopropyl phosphate, diisopropyl phosphate, or a mixture of two or more of the foregoing.

5. The method of claim 4, in which the salt is a potassium salt.

6. The method of claim 1, in which the antistatic agent is an alkali metal or ammonium salt of isobutyl phosphate, diisobutyl phosphate, or a mixture thereof.

7. The method of claim 6, in which the salt is a potassium salt.

8. The method of claim 1, in which the oxidizing gas plasma comprises a hydrogen peroxide gas plasma.

9. The method of claim 1, in which the nonwoven web is a meltblown web.

10. The method of claim 9, in which the meltblown web is a component of a laminate.

11. The method of claim 10, in which the meltblown web is between and bonded to two spunbond webs.

12. The method according to claim 1 wherein said alkali metal or ammonium salt of a mono- or di-$C_3$-alkyl phosphate has a $C_3$-alkyl moiety comprising an alkyl group containing three carbon atoms, each of said carbon atoms substituted with hydroxy groups.

13. A fibrous material comprising:

a gas-permeable, water-impermeable nonwoven web coated-with from about 0.005 to about 3 percent by weight, based on the weight of the web, of an antistatic agent selected from the group consisting of an alkali metal or ammonium salt of a mono- or di-$C_3$-alkyl phosphate in which the $C_3$-alkyl moiety is an alkyl group containing three carbon atoms at least one of said carbon atoms substituted with an hydroxy group, a mixture of two or more of such salts, an alkali metal or ammonium salt of a β-carbon substituted alkyl phosphate, a di(β-carbon substituted alkyl) phosphate, or a mixture of two or more of the foregoing, wherein the β-carbon substituted alkyl group contains from four to about seven carbon atoms;

wherein the sterilized coated nonwoven web is, after exposure to an oxidizing gas plasma free of a malodor and has a hydrohead value as measured by Method 5514 of Federal Test Method Standard No. 191A after exposure to the oxidizing gas plasma which is at least 50 percent of the hydrohead value of the coated water-impermeable nonwoven web before exposure to the oxidizing gas plasma.

14. A barrier fabric comprising the fibrous material of claim 13.

15. A sterilization wrap comprising the fibrous material of claim 13.

16. A surgical garment comprising the fibrous material of claim 13.

17. A medical procedure pack comprising:

a fluid permeable container having an exterior and an interior;

one or more items to be sterilized which are present in the interior of the container; and one or more layers of sterilization wrap surrounding the exterior of the container in a sealing relationship;

in which the sterilization wrap comprises a gas-permeable, water-impermeable nonwoven web coated with from about 0.005 to about 3 percent by weight, based on the weight of the web, of an antistatic agent selected from the group consisting of an alkali metal or ammonium salt of a mono- or di-$C_3$-alkyl phosphate in which the $C_3$-alkyl moiety is an alkyl group containing three carbon atoms at least one of said carbon atoms substituted with an hydroxy group, a mixture of two or more of such salts, an alkali metal or ammonium salt of a β-carbon substituted alkyl phosphate, a di(β-carbon substituted alkyl) phosphate, or a mixture of two or more of the foregoing, wherein the β-carbon substituted alkyl group contains from four to about seven carbon atoms, wherein, after exposure of the coated water-impermeable nonwoven web to an oxidizing gas plasma, the sterilized, coated nonwoven web is free of a malodor and has a hydrohead value as measured by Method 5514 of Federal Test Method Standard No. 191A after exposure to the oxidizing gas plasma which is at least 50 percent of the hydrohead value of the coated water-impermeable nonwoven web before exposure to the oxidizing gas plasma.

18. The medical procedure pack of claim 17, in which the pack has been exposed to an oxidizing gas plasma.

19. A medical procedure pack comprising:

a liquid-impermeable container having an exterior and an interior, in which at least a portion of the container comprises a gas-permeable, water-impermeable nonwoven web; and one or more items to be sterilized which are present in the interior of the container;

in which the nonwoven web is coated with from about 0.005 to about 3 percent by weight, based on the weight of the web, of an antistatic agent selected from the group consisting of an alkali metal or ammonium salt of a mono- or di-$C_3$-alkyl phosphate in which the $C_3$-alkyl moiety is an alkyl group containing three carbon atoms at least one of said carbon atoms substituted with an hydroxy group, a mixture of two or more of such salts, an alkali metal or ammonium salt of a β-carbon substituted alkyl phosphate, a di(β-carbon substituted alkyl) phosphate, or a mixture of two or more of the foregoing, wherein the β-carbon substituted alkyl group contains from four to about seven carbon atoms, wherein after exposure of the coated water-impermeable nonwoven web to an oxidizing gas plasma, the sterilized, coated nonwoven web is free of a malodor and has a hydrohead value as measured by Method 5514 of Federal Test Method Standard No. 191A after exposure to the oxidizing gas plasma which is at least 50 percent of the hydrohead value of the coated water-impermeable nonwoven web before exposure to the oxidizing gas plasma.

20. The medical procedure pack of claim 19, in which the pack has been exposed to an oxidizing gas plasma.

* * * * *